(12) United States Patent
Judy et al.

(10) Patent No.: US 9,604,039 B2
(45) Date of Patent: Mar. 28, 2017

(54) UNOBSTRUCTING MICRODEVICES FOR SELF-CLEARING IMPLANTABLE CATHETERS

(75) Inventors: Jack W. Judy, Los Angeles, CA (US);
Hyowon Lee, Los Angeles, CA (US);
Marvin Bergsneider, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 743 days.

(21) Appl. No.: 13/164,587

(22) Filed: Jun. 20, 2011

(65) Prior Publication Data

US 2011/0313340 A1    Dec. 22, 2011

Related U.S. Application Data

(60) Provisional application No. 61/356,519, filed on Jun. 18, 2010.

(51) Int. Cl.
*A61M 1/00* (2006.01)
*A61M 27/00* (2006.01)
*A61M 25/00* (2006.01)

(52) U.S. Cl.
CPC ........ *A61M 27/006* (2013.01); *A61M 25/007* (2013.01)

(58) Field of Classification Search
USPC ............................................................ 604/8
See application file for complete search history.

(56) References Cited

U.S. PATENT DOCUMENTS 5,645,564 A * 7/1997 Northrup ......... A61B 17/12022
606/205
5,647,367 A * 7/1997 Lum ....................... A61B 8/12
600/463

(Continued)

FOREIGN PATENT DOCUMENTS

WO    2006122168 A2    11/2006

OTHER PUBLICATIONS

Dobkin and Zuraw (2003). Principles of Chemical Vapor Deposition. Dordrecht Boston: Kluwer Academic Publishers, 2003 (ISBN Jan. 4020-1248-9.*

(Continued)

*Primary Examiner* — Adam Marcetich
*Assistant Examiner* — Guy K Townsend
(74) *Attorney, Agent, or Firm* — O'Banion & Ritchey LLP; John P. O'Banion

(57) ABSTRACT

A self-clearing actuator configured to be positioned in a pore providing fluid communication into a central lumen of a ventricular catheter body is described. The actuator extends into a central bore via a cantilever beam having a first end emanating at the central bore and a second end terminating at the actuator, wherein the actuator is configured to reciprocate within the central bore between a first position extending downward at an angle into the central bore and a second position substantially at or above the external surface of the catheter. The cantilever beam is stressed, e.g. via a composite compress layer, such that it is preloaded to nominally curve downward to extend the actuator into the second position. The actuator is preferably a magnet responsive to magnetic field such that the magnetic field drives the actuator toward the first position.

9 Claims, 15 Drawing Sheets

(56) References Cited

U.S. PATENT DOCUMENTS

| | | | | |
|---|---|---|---|---|
| 5,701,901 | A * | 12/1997 | Lum | A61B 8/12 600/462 |
| 5,722,989 | A * | 3/1998 | Fitch | A61B 17/12022 606/205 |
| 5,771,902 | A * | 6/1998 | Lee | A61B 17/12022 128/897 |
| 5,779,643 | A * | 7/1998 | Lum | A61B 8/12 29/25.35 |
| 5,993,463 | A * | 11/1999 | Truwit | A61B 90/11 606/129 |
| 6,206,890 | B1 * | 3/2001 | Truwit | A61B 90/11 600/417 |
| 6,267,770 | B1 * | 7/2001 | Truwit | A61B 90/11 600/417 |
| 6,368,329 | B1 * | 4/2002 | Truwit | A61B 90/11 606/129 |
| 6,692,456 | B1 * | 2/2004 | Eppstein | A61B 10/0045 600/309 |
| 6,752,812 | B1 * | 6/2004 | Truwit | A61B 90/11 606/1 |
| 2004/0039342 | A1 * | 2/2004 | Eppstein | A61M 37/0015 604/200 |
| 2006/0009785 | A1 * | 1/2006 | Maitland | A61B 17/221 606/113 |
| 2008/0172073 | A1 * | 7/2008 | Boyden | A61F 2/02 606/155 |
| 2008/0262341 | A1 * | 10/2008 | Boyden | A61F 2/02 600/424 |
| 2008/0281250 | A1 * | 11/2008 | Bergsneider | A61M 25/007 604/9 |
| 2009/0105794 | A1 * | 4/2009 | Ziarno | A61F 2/2436 607/120 |
| 2009/0264810 | A1 * | 10/2009 | Eppstein | A61M 37/0015 604/20 |

OTHER PUBLICATIONS

Lee. S.A. et al. —"Functional Evaluation of Magnetic Microactuators for Removing Biological Accumulation: An In Vitro Study"—30th Annual Int. IEEE EMBS Conf., Vancouver, British Columbia, Canada, Aug. 20-24, pp. 947-950 , 2008.

* cited by examiner

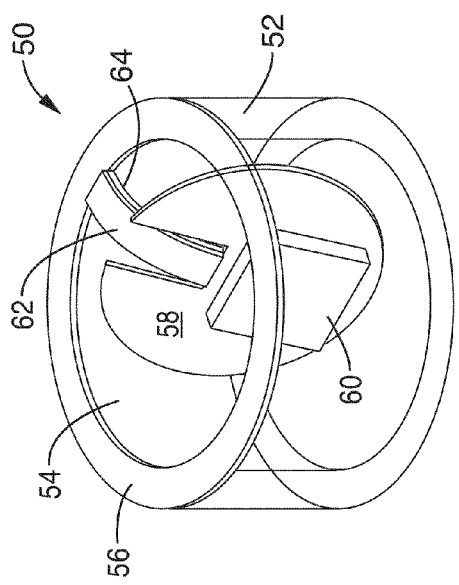
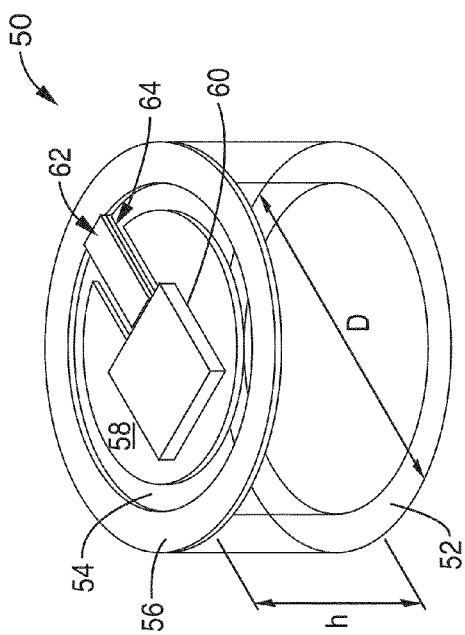
FIG. 5A
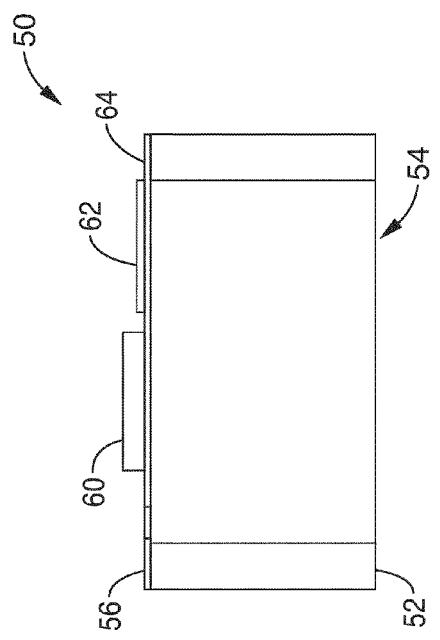
FIG. 5B

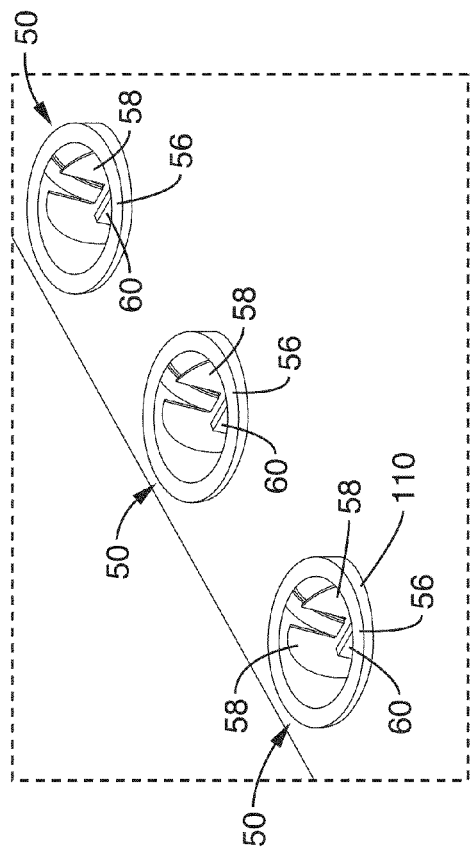
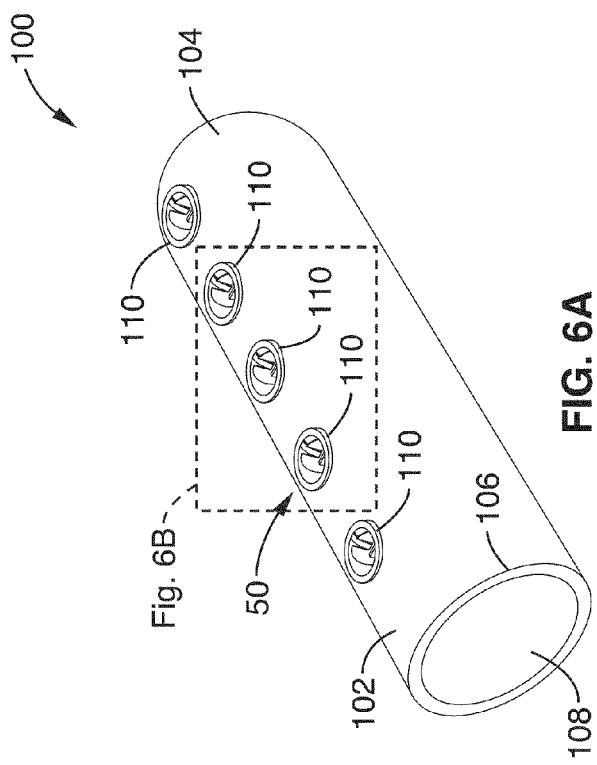

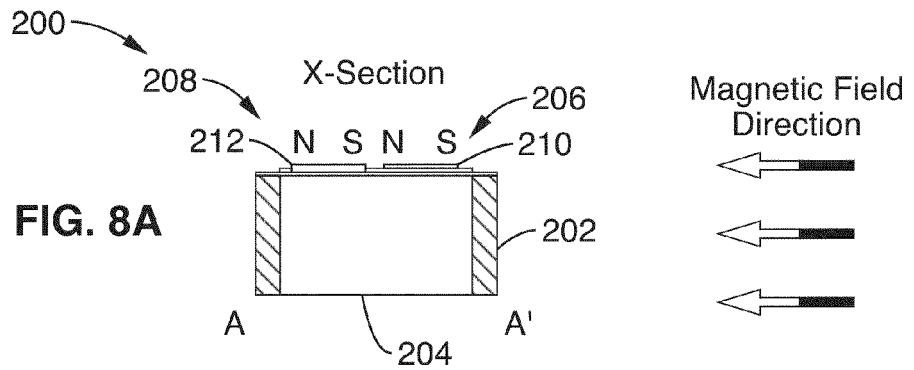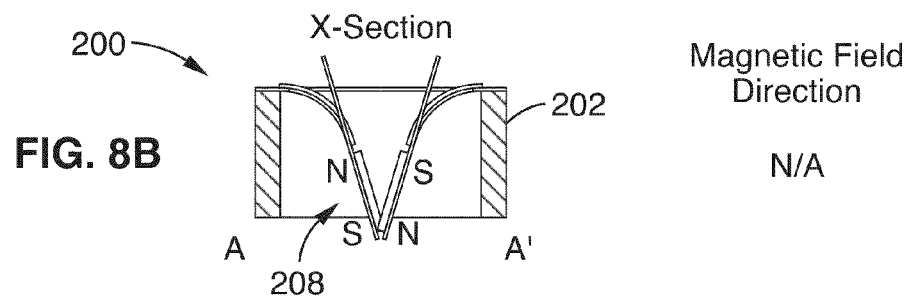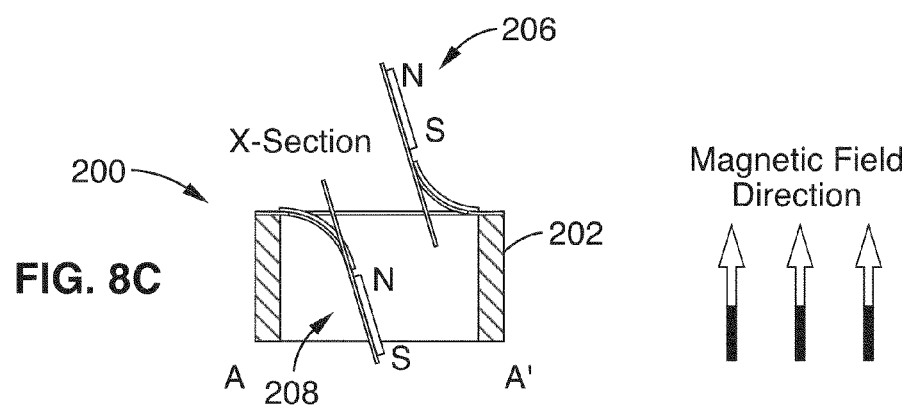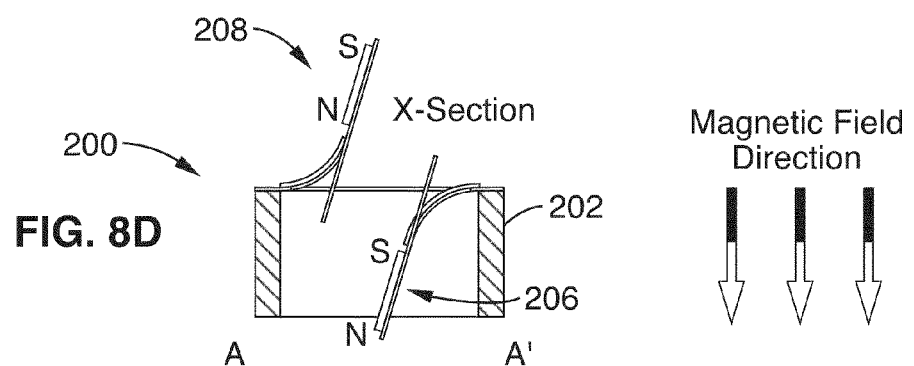

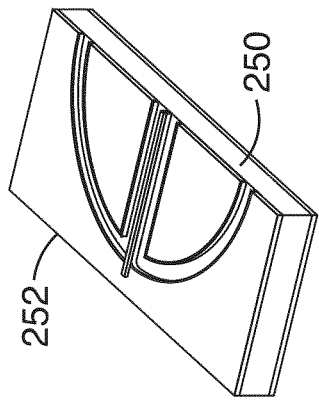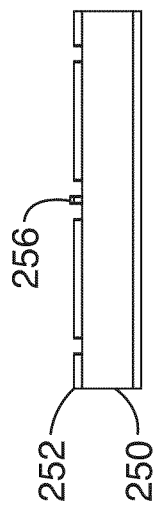
FIG. 12C
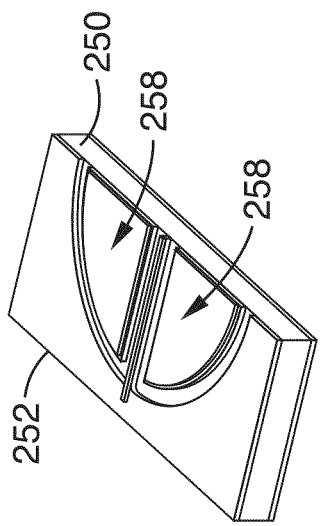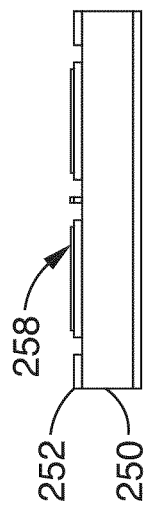
FIG. 12D

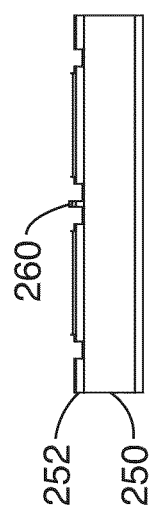
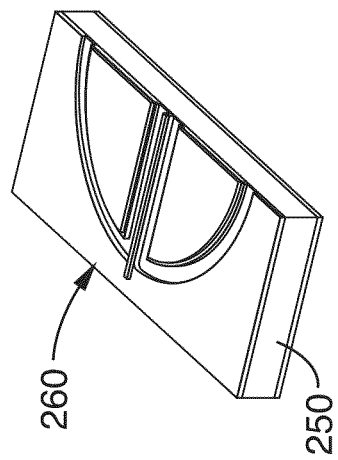
FIG. 12E
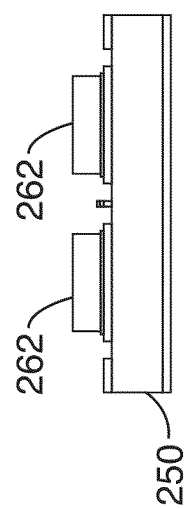
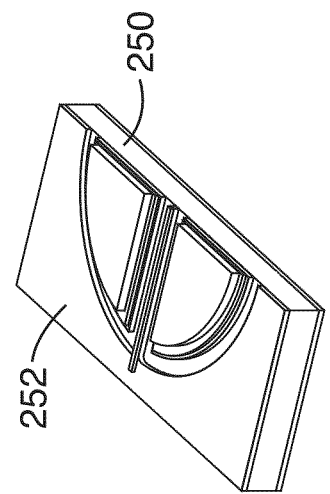
FIG. 12F

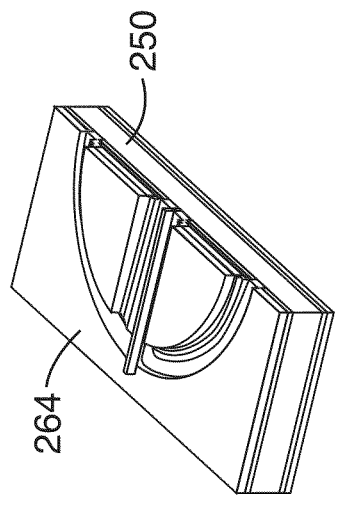
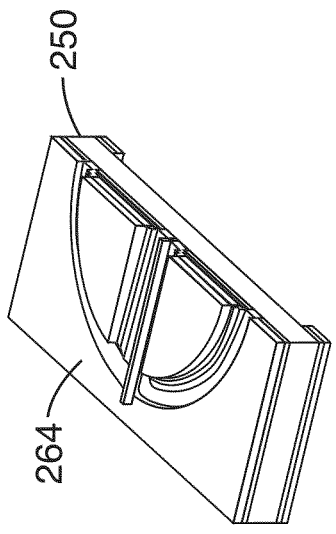
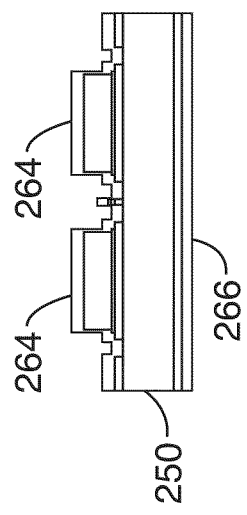
FIG. 12G
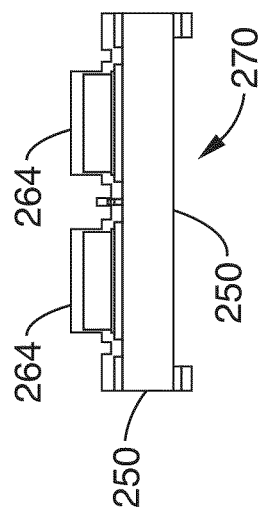
FIG. 12H

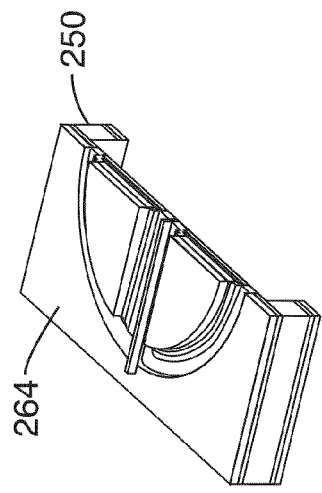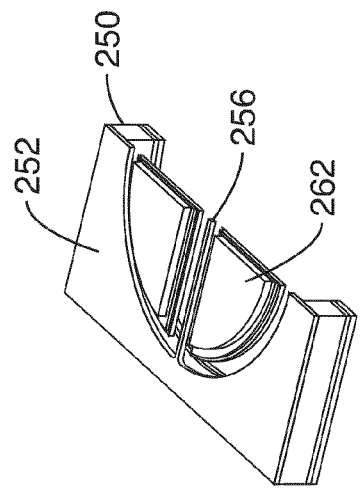
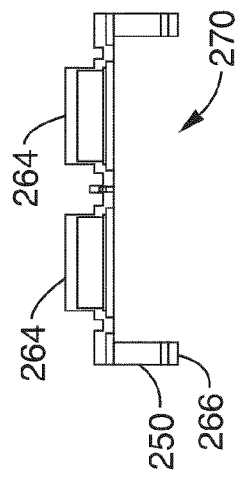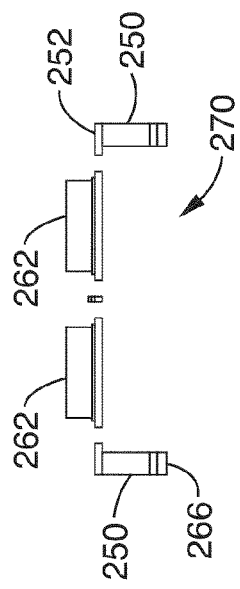
FIG. 12I
FIG. 12J

UNOBSTRUCTING MICRODEVICES FOR SELF-CLEARING IMPLANTABLE CATHETERS

CROSS-REFERENCE TO RELATED APPLICATIONS

This application claims priority from U.S. provisional patent application Ser. No. 61/356,519 filed on Jun. 18, 2010, incorporated herein by reference in its entirety.

STATEMENT REGARDING FEDERALLY SPONSORED RESEARCH OR DEVELOPMENT

This invention was made with Government Support under NS062324, awarded by the National Institutes of Health. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to implantable catheters, and more particularly to self-clearing catheters.

2. Description of Related Art

One in every 500 newborns is afflicted by hydrocephalus, a condition characterized by an abnormal accumulation of cerebrospinal fluid (CSF) due to an imbalance between cerebrospinal fluid production and absorption. In addition, hydrocephalus may also be acquired later in life due to incidents such as head trauma or tumor development. Fortunately, treatments have greatly increased the probability for hydrocephalic patients to achieve normal intelligence and to lead a normal life.

Implanted medical catheters are now an integral part of clinical care. Over 25,000 shunt operations are completed each year in the U.S. alone. Patients who receive implanted shunts are dependent on the device functioning properly.

However, many chronically implanted catheter systems are often plagued with reduced performance due to the prolonged accumulation of biological debris. For the neurological disorder of hydrocephalus, obstruction of the shunt tubing that diverts cerebrospinal fluid (CSF) from the brain is one of the most commonly occurring complications, which can result in a catastrophic shunt failure that could inflict serious bodily harm to the patient.

A malfunctioning (or obstructed) shunt can be a life-threatening condition. On average, 85% of people with shunts have at least two shunt-revision surgeries in their lifetime. A minority of patients are plagued with recurrent shunt obstructions and may undergo over 100 shunt revisions. Each successive shunt revision may cause brain injury and increases the risk of shunt infection. Not only are shunt-replacement surgeries a cause of morbidity and stress for patients and families, but they also impose economic burdens on the patient and society.

FIG. 1 illustrates a system 10 having shunt tubing to divert cerebrospinal fluid (CSF) from brain 14. System 10 generally comprises a ventricular catheter 20 positioned within affected ventricle 14. The ventricular catheter 20 is coupled to tubing 24 via a valve 22. The tubing 24 runs the length of the torso to drain within the low abdomen 28. Shunt obstructions can occur at various locations around the implanted system 10. Certain locations, such as the distal end of the catheter 26, the valve 22, and the ventricular catheter 20, however, are most often implicated.

Although recent improvements in valve designs and antimicrobial coatings have reduced the occurrence of obstructions at the valve 22 and the distal end of the shunt 26, methods to prevent the ventricular catheter 20 obstruction still remain elusive.

There are multiple recognized causes of the obstruction at the ventricular end of the shunt system, the primary ones being summarized below:

1. Gradual accumulation of cells in flow pores: FIG. 2 illustrates a currently available ventricular shunt system using a ventricular catheter 20 having a plurality of intake pores 30 at end 32 of the catheter. As seen further in the cross-sectional view of FIG. 3, cells 36 may accumulate in and around intake pore 30 to partially and then fully occlude the opening 30. Hydrocephalus often results in an increased numbers of cells in the patients' CSF (pleocytosis). Similar pathology can be found in patients with chronic meningitis, and it is thought to be one of the main causes of shorter shunt half-lives for these patients. Indeed, non-pleocytic CSF does have lower cellular concentration. However, even in hydrocephalus patients without pleocytosis, the shunt system moves hundreds of millions of cells to through its catheter pores in its lifetime such that the cellular occlusion is almost a certain eventuality. As such, the cellular occlusion is thought to be one of the main causes of shunt malfunction in hydrocephalus patients.

2. Ventricular collapse due to excess drainage: Ventricular collapse following shunting procedures has been associated with shunt obstruction. A primary focus of valve 22 design has been to limit excessive drainage and therefore prevent the collapse of the ventricles 14. Although the incorporation of valves with an adjustable opening differential pressure that control the rate of CSF flow have been touted to maintain an ideal ventricular size and intracranial pressure, these goals have not been consistently achieved clinically. The mechanism by which obstruction occurs with ventricular collapse is related to the direct apposition of ependymal and/or choroid plexus tissue with the ventricular catheter tip. The close proximity to the ependymal wall provides abundant supply of cells to accumulate on the ventricular catheter pores. Despite advances in valve technologies, ventricular collapse continues to be an increased risk of shunt obstruction.

3. Choroid plexus tissue migration and ingrowth: Choroid plexus tissue migration occurs in situations where the catheter flow holes are in close proximity with the choroid. The suctioning effect, which is inherent in many shunt designs, can draw the choroid tissue directly into the catheter pores. FIG. 2 shows a prior art flanged catheter tip 20b having a plurality of radial flanges 34 at the site of the apertures 30, which was introduced with the goal of preventing the choroid tissue from accessing the flow holes 30. The clinical experience with this design, however, has been mixed. Proximal catheter obstructions have not been prevented and the reason is not clear. Assuming choroid tissue was indeed impeded, cells freely floating in CSF presumably led to the obstruction. Some studies have suggested that optimal placement of the catheter tip is at a location that is out of the reach of the choroid plexus. Anatomically, this placement goal is very difficult to achieve with current catheter designs. With better catheter designs and judicious use of endoscopy, this placement goal may be achieved.

Cellular occlusion is thought to be one of the main causes of failure for the chronically implanted catheters in hydrocephalus patients. Pathological studies have shown that the cellular composition of catheter obstruction consists mainly of: red blood cells, inflammatory cells, and proteins. Though not commonly present in CSF, red blood cells are often introduced into the CSF due to hemorrhaging that occurs during shunt placement surgery. Thus, in a long-term scale, red blood cells do not have substantial impact on obstruction formation. Red blood cells, however, are susceptible to coagulation, which could result in larger body of mass that may ultimately obstruct catheter pores. Inflammatory cells and other associated proteins are identified as the main components of the cellular accumulation. With introduction of foreign material (catheter) into the brain, the white blood cells (leukocytes) undergo a delayed hypersensitivity reaction that leads to increased cellular adhesion. A proteinaceous layer that forms on the surface of the catheter facilitates this process by allowing formation of arginine-glycine-glutamic acid (RGD) receptor-ligand complex that recruits more leukocytes to the silicone surface.

Biomedical approaches, such as use of a silicone elastomer, grafting, hydrophilic, lubricious hydrogel onto the silicone surface, and drug-eluting catheters, have yet to display consistent performance over long period of time.

Microfabricated self-clearing catheters have previously been used (U.S. Patent No. 2008/0281250) to incorporate microfabricated magnetic actuators into conventional ventricular catheters to combat cellular occlusion. The magnetic microactuator produces out-of-plane movements to allow for disruption or prevention of biological accumulation at the flow pores. However, one major caveat of this approach is that the device must reside within the catheter pore, and thus is prone to cause additional hindrance to the normal flow of CSF. Because this torsional-microactuator-design maintains a horizontal rest position, it greatly reduces the open pore area at rest and occludes much of the catheter pore while in this state.

Accordingly, an object of the present invention is a system and fabrication process for magnetic microactuators that stay clear of the catheter pore while at rest.

BRIEF SUMMARY OF THE INVENTION

By way of example, and not of limitation, the present invention comprises a self-clearing actuator configured to be positioned in a pore providing fluid communication into the central lumen of the ventricular catheter body. In one embodiment, the actuator may extend into a central bore via a cantilever beam having a first end emanating at the central bore and a second end terminating at the actuator, wherein the actuator is configured to reciprocate within the central bore between a first position extending downward at an angle into the central bore and a second position substantially at or above the external surface of the catheter. The cantilever beam may be stressed, e.g. via a composite compress layer, such that it is preloaded to nominally curve downward to extend the actuator into the second position. The actuator may comprise a magnet responsive to magnetic field such that the magnetic field drives the actuator toward the first position.

An aspect of the invention is an apparatus for self-clearing a flow pore in a human implant, comprising: a housing configured to be disposed in a flow pore of the implant; said housing comprising a central bore spanning between an upper surface and a lower surface of the housing, the central bore providing fluid communication into said flow pore; an actuator plate extending from the upper surface of the housing into the central bore via a cantilever beam; the cantilever beam having a first end emanating at the central bore and a second end terminating at the actuator plate; the actuator plate configured to reciprocate within the central bore between a first position extending downward at an angle into the central bore and a second position substantially at or above the upper surface of the housing; wherein the cantilever beam is stressed such that it is preloaded to nominally curve downward to extend the actuator plate in the second position; and wherein the actuator plate comprises a magnet responsive to magnetic field such that the magnetic field drives the actuator plate toward the first position.

Another aspect is a self-clearing ventricular catheter, comprising: a catheter body comprising a central lumen extending from a proximal end to a distal end of the catheter; one or more pores providing fluid communication into the central lumen of the catheter body; wherein the one or more pores comprise a central bore extending from an external surface of the catheter to an internal surface of the catheter; the one or more pores comprise a self-clearing actuator; the actuator extending into the central bore via a cantilever beam; the cantilever beam having a first end emanating at the central bore and a second end terminating at the actuator; the actuator configured to reciprocate within the central bore between a first position extending downward at an angle into the central bore and a second position substantially at or above the external surface of the catheter; wherein the cantilever beam is stressed such that it is preloaded to nominally curve downward to extend the actuator into the second position; and wherein the actuator comprises a magnet responsive to magnetic field such that the magnetic field drives the actuator toward the first position.

Another aspect is a shunt system configured for diverting cerebrospinal fluid (CSF) from a ventricle of the brain, comprising: a ventricular catheter having proximal end and a distal end; tubing coupled to the distal end of the ventricular catheter; said tubing having a length sufficient to extend from the ventricle into an abdominal region of the patient; the ventricular catheter comprising a central lumen extending from a proximal end to a distal end of the catheter; the ventricular catheter comprising one or more pores each comprising a central bore extending from an external surface of the catheter to an internal surface of the catheter; the one or more pores providing fluid communication of CSF from the ventricle into the central lumen of the catheter; the one or more pores comprise a self-clearing actuator; the actuator extending into the central bore via a cantilever beam; the cantilever beam having a first end emanating at the central bore and a second end terminating at the actuator; the actuator configured to reciprocate within the central bore between a first position extending downward at an angle into the central bore and a second position substantially at or above the external surface of the catheter; wherein the cantilever beam is stressed such that it is preloaded to nominally curve downward to extend the actuator into the second position; and wherein the actuator comprises a magnet responsive to magnetic field such that the magnetic field drives the actuator toward the first position.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 5A shows perspective and side views of a cantilever-based magnetic microactuator of the present invention in a pre-release (flat) configuration.

FIG. 5B shows perspective and side views of the cantilever-based magnetic microactuator of FIG. 5A in a post-release (bent) configuration FIG. 6 is a 3D illustration of the proposed self-clearing catheter integrated with self-clearing microactuators of FIG. 5A.

FIG. 8A through FIG. 8D show cross-sectional views of the microactuator 200 of FIG. 7A in various configurations.

FIG. 12A through FIG. 12J show schematic diagram s of an exemplary fabrication process for creating a round single-cantilever microactuator similar to that shown in FIG. 5A and FIG. 5B.

DETAILED DESCRIPTION OF THE INVENTION

The methods and systems of the present invention are directed to a microactuator having a cantilever-based actuation device that rests away from the pore surface to allow normal flow of bodily fluids (e.g. CSF) though the catheter in the absence of magnetic field.

Figure 1:
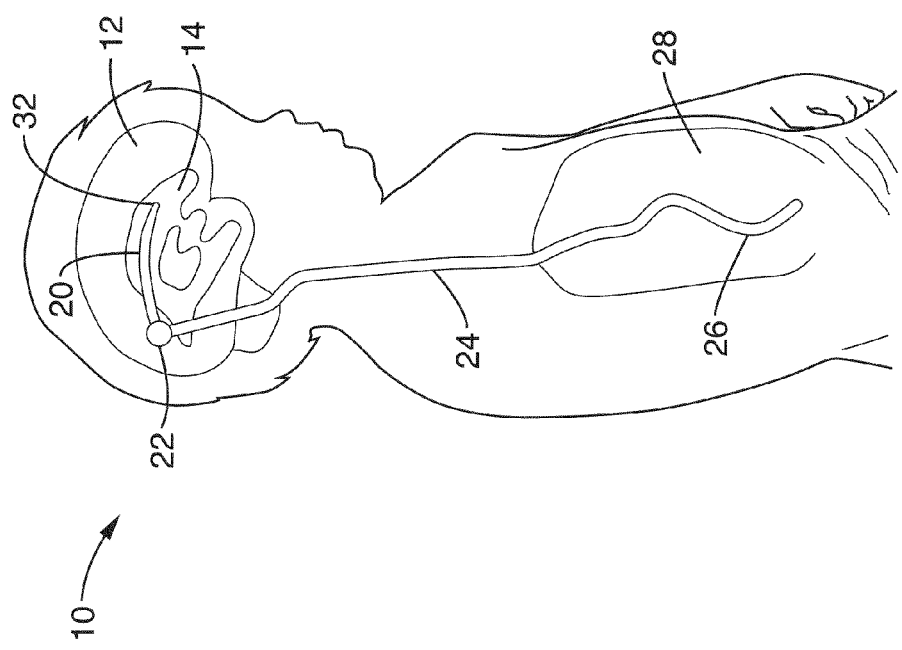
FIG. 1 illustrates a schematic diagram of a shunt tubing system to divert cerebrospinal fluid (CSF) from the brain.
Figure 2:
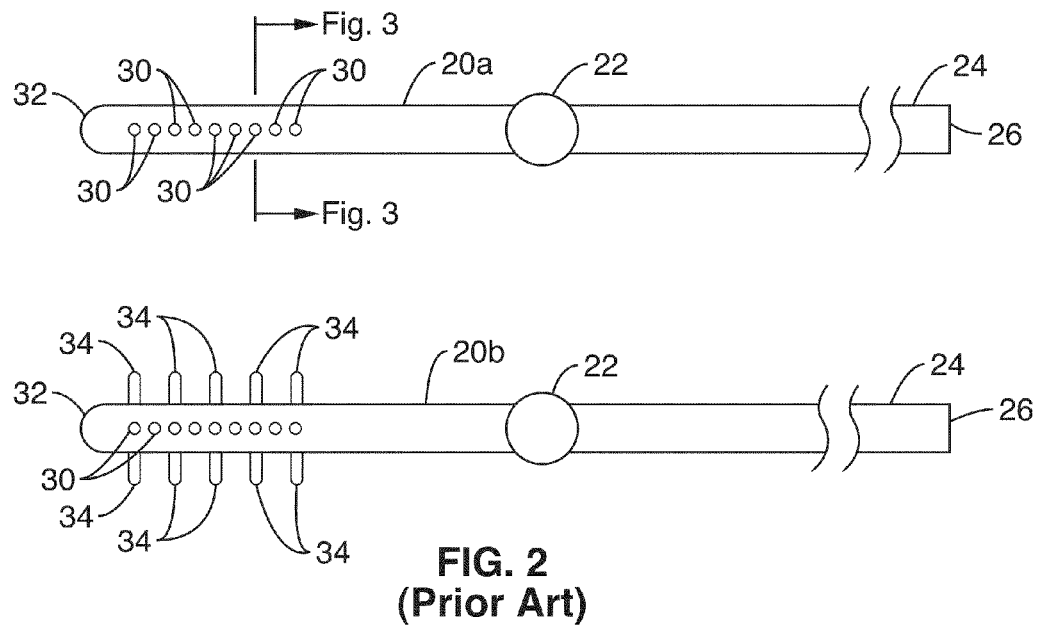
FIG. 2 shows two prior art ventricular catheters
Figure 3:
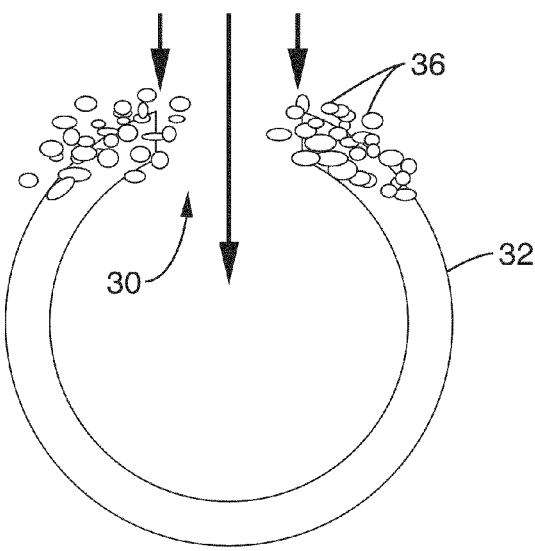
FIG. 3 is a cross-sectional view of one of the ventricular catheters of FIG. 2 with partial occlusion.
Figure 4:
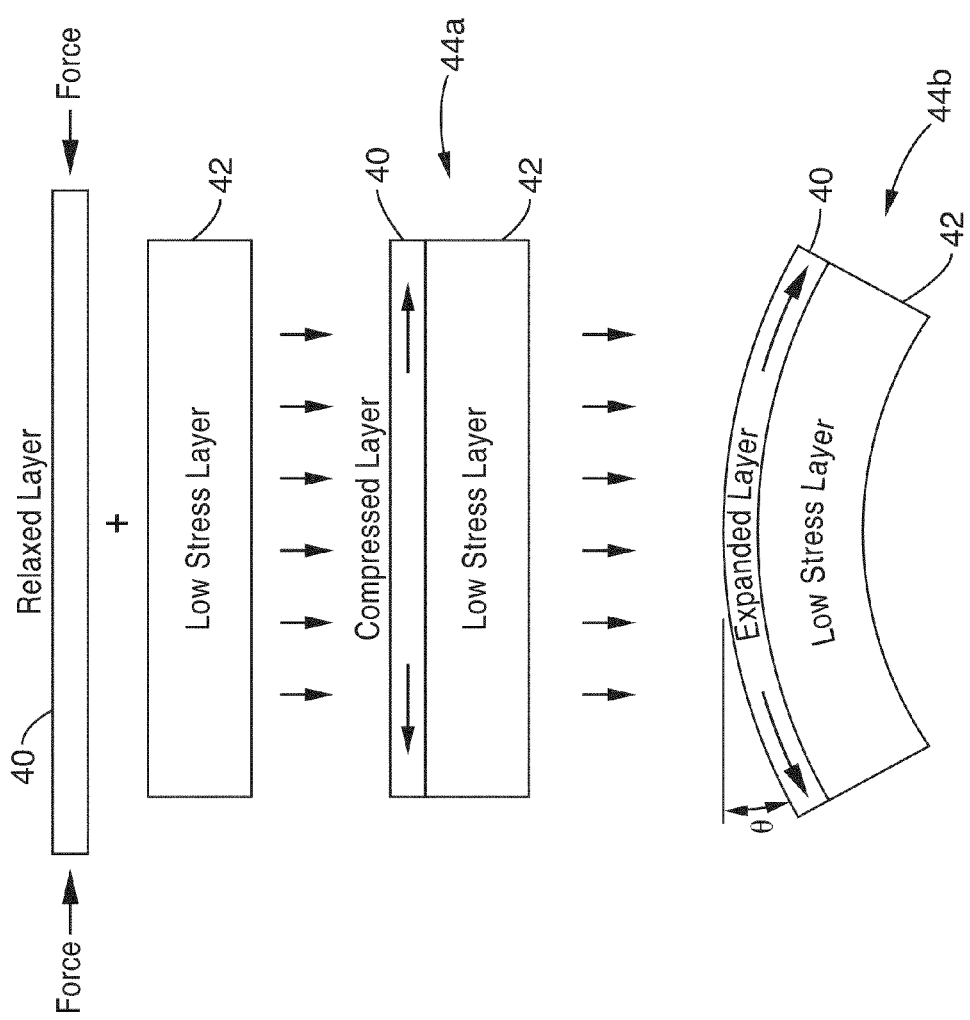
FIG. 4 shows a diagram illustrating bending due to stress mismatch in a bimorph.

Conventional cantilevers are made of single homogeneous material, which generates a flat released structure. However, as shown in FIG. 4, a bimorph of two different intrinsic stress levels bends up or down upon release. FIG. 4 is an illustration of bending due to stress mismatch in a bimorph. A relaxed layer 40 (e.g. of PECVD $Si_xN_y$) is compressed with an applied force and deposited on to a low-stress structural substrate layer 42 (e.g. LPCVD $Si_xN_y$) to form composite 44A. This causes a bending of the composite material to form a nominal bent shape 44B to relieve the stress. The composite structure 44B may be configured to have a desired nominal bending angle θ.

FIG. 5A shows perspective and side views of a cantilever-based magnetic microactuator 50 in a pre-release (flat) configuration, and FIG. 5B shows perspective and side views of the cantilever-based magnetic microactuator 50 in a post-release (bent) configuration. FIG. 5A shows the flat device configuration before being released from the substrate. FIG. 5 B shows the stress-induced deflected rest position after release.

The microactuator 50 comprises a cylindrical housing 52 having an opening 54 to promote free range of motion of actuator plate 58. As shown in the pre-release configuration of FIG. 5A, actuator plate 58 is positioned over recess 54 generally in line with upper surface 56 of housing 52. The actuator plate 58 is coupled to the upper surface 56 via a thin cantilever beam 64. A compressively stressed layer 62 is disposed on the beam 64 to form a pre-loaded composite, such that the beam 64 is naturally biased to curve downward (e.g. post-release configuration shown in FIG. 5B) absent any intervening force.

In a preferred embodiment, layer 64 comprises silicon nitride produced by a plasma-enhanced chemical vapor deposition (PECVD), with a very high intrinsic stress of approximately 1-GPa. By controlling the parameters of bimorph interaction (e.g. thickness of beam 62 and layer 64, etc., the angle of post-release bend of cantilever beam 64 can be readily controlled. Thus, optimum angle of post-release bend may be varied to accommodate the flow of CSF through pores with by allowing the microactuators 50 to be deflected inwards at different angles Actuator plate 58 comprises a magnet 60 that is responsive to a magnetic force, such that a magnetic force may be applied to the counteract the curved bias of the compressively stressed beam 64. With the magnetic force applied, the beam 64 is deflected back to the flat pre-release configuration shown in FIG. 5A. Thus, magnetic forces may be cycled to generate a clearing motion and thus inhibit occlusion of the pore from biological debris. Periodic actuation of the magnetic microactuators 50 acts to physically remove any cellular accumulation and refreshes the pore to its initial clear state. Initial testing showed that such microactuators can be subjected to over 250 million cycles of actuation without showing any significant change in their mechanical properties.

The microactuator 50 may be sized to have a height h and diameter D sized to be inserted in a desired ventricular catheter pore. FIG. 6 illustrates an exemplary ventricular catheter 100 having a plurality of flow pores 110, each supporting a microactuator 50 for self-clearing of the pores 110. The microactuators 50 are recessed into the body 102 of the ventricular catheter 100 at each pore 110 location such that the upper surface 56 of the housing 52 is flush or just above the outer surface of the catheter body 102. The microactuators 50 are shown in FIG. 6 with the actuator plates 58 in a post release configuration to allow for passage of fluids into the pores 110, into the central cavity 108 and out distal end 10 of the catheter body 104.

The configuration shown in FIG. 5A, FIG. 5B and FIG. 6 show a cylindrical microactuator 50 having an outer diameter D closely matching the diameter of the pores 110 such that the microactuator 50 can be press fit into (e.g. interference fit) or adhered to the catheter body 104. It is also appreciated that the microactuators 50 and pores 110 may comprise a number of different configurations, such as that rectangular configuration described below with respect to FIG. 7A through FIG. 8.

Figure 7A:
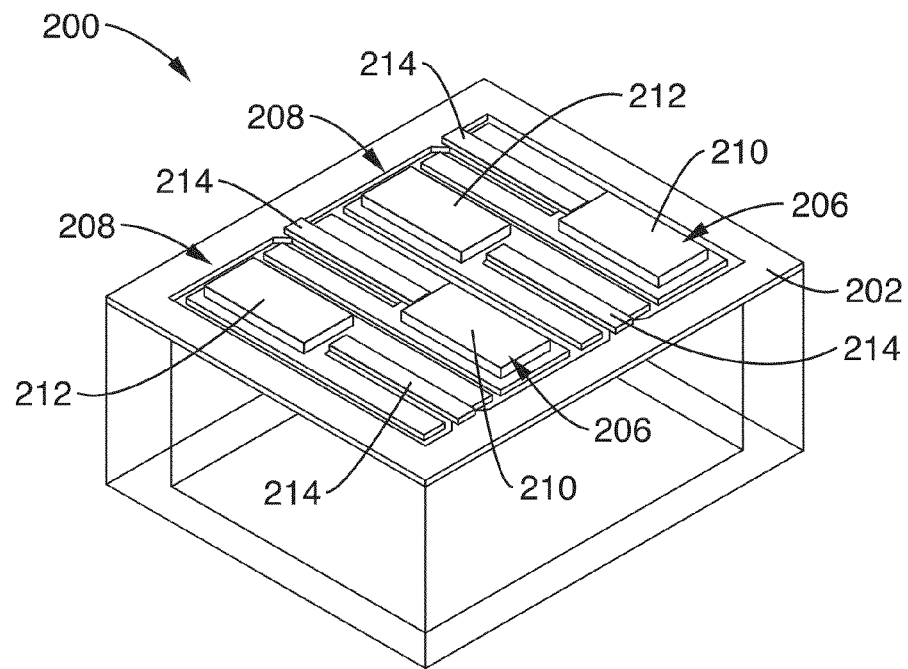
FIGS. 7A and 7B are perspective views of schematic illustrations of interdigitated cantilever-based magnetic microactuators in pre-release (FIG. 7A) and post release (FIG. 7B) configurations.
Figure 7B:
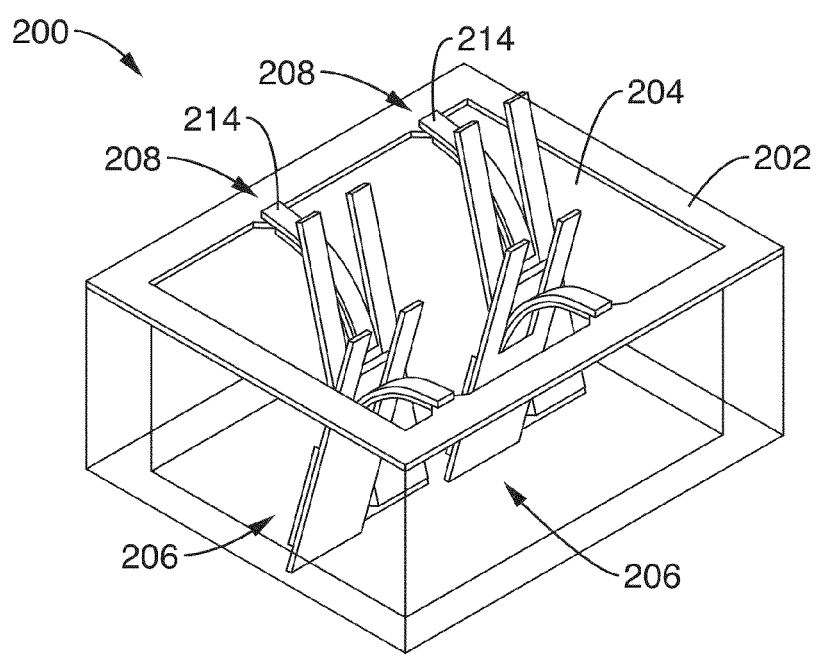

FIG. 7A and FIG. 7B are perspective views of schematic illustrations of interdigitated cantilever-based magnetic microactuators 200 in pre-release (FIG. 7A) and post release (FIG. 7B) configurations. Microactuators 200 comprise an array of individually operable actuation plates 206, 208, each having respective magnets 210, 212, disposed on composite cantilever beams 214. The array of actuation plates 206, 208 fit within recess 204 of housing 202 so that multiple actuators may reside within a single catheter pore (e.g. pore 110 sized and shaped to fit the rectangular housing 202).

Cantilever beams 214 comprise compressively stressed layer that is disposed on the beam to form a pre-loaded composite, such that the beams 214 are naturally biased to curve downward (see FIG. 8B).

The multiple microactuators 210, 212 arranged in an interdigitated manner such that in the presence of an ac magnetic field, the interdigitated devices will alternate directions to provide more dynamic action at the pore to clear the occlusion more effectively.

FIG. 8A through FIG. 8D show cross-sectional views of the microactuator 200 of FIG. 7A and FIG. 7B. The magnets 210, 212 cantilever actuator plates 206,208 are magnetized in opposite directions (e.g. different N-S orientations) prior to release. Thus, application of a lateral application of magnetic field 220 maintains the actuator plates 206, 208 in the same plane at the top of the housing 202. In the absence or release of a magnetic field 220, as shown in FIG. 8B, the actuator plates 206, 208 will then bend into the lumen 204 of the pore.

In the presence of an upward magnetic field 222 as shown in FIG. 8C, the actuator plates 206 on the right side of the housing 202 will actuate up and the actuator plates 208 on the left side of the housing 202 will actuate down to align their magnetic poles to that of the magnetic field 222.

In the presence of a downward magnetic field 224 as shown in FIG. 8D, the actuator plates 206 on the right side of the housing 202 will actuate down and the actuator plates 208 on the left side of the housing 202 will actuate up to align their magnetic poles to that of the magnetic field 224.

Thus, the microactuator 200 may be cycled through two or more of the four configurations shown in FIG. 8A through FIG. 8D to provide clearing of the pore.

The response of the cantilever beams (beam 64 in FIG. 5A and FIG. 5B and beams 214 in FIG. 7A and FIG. 7B) may be finely controlled using dimensional constraints during fabrication, in particular, the relationship between angular deflection and the silicon-nitride beam layer thickness as a function of the thickness of stress-inducing PECVD silicon-nitride layer.

Figure 9:
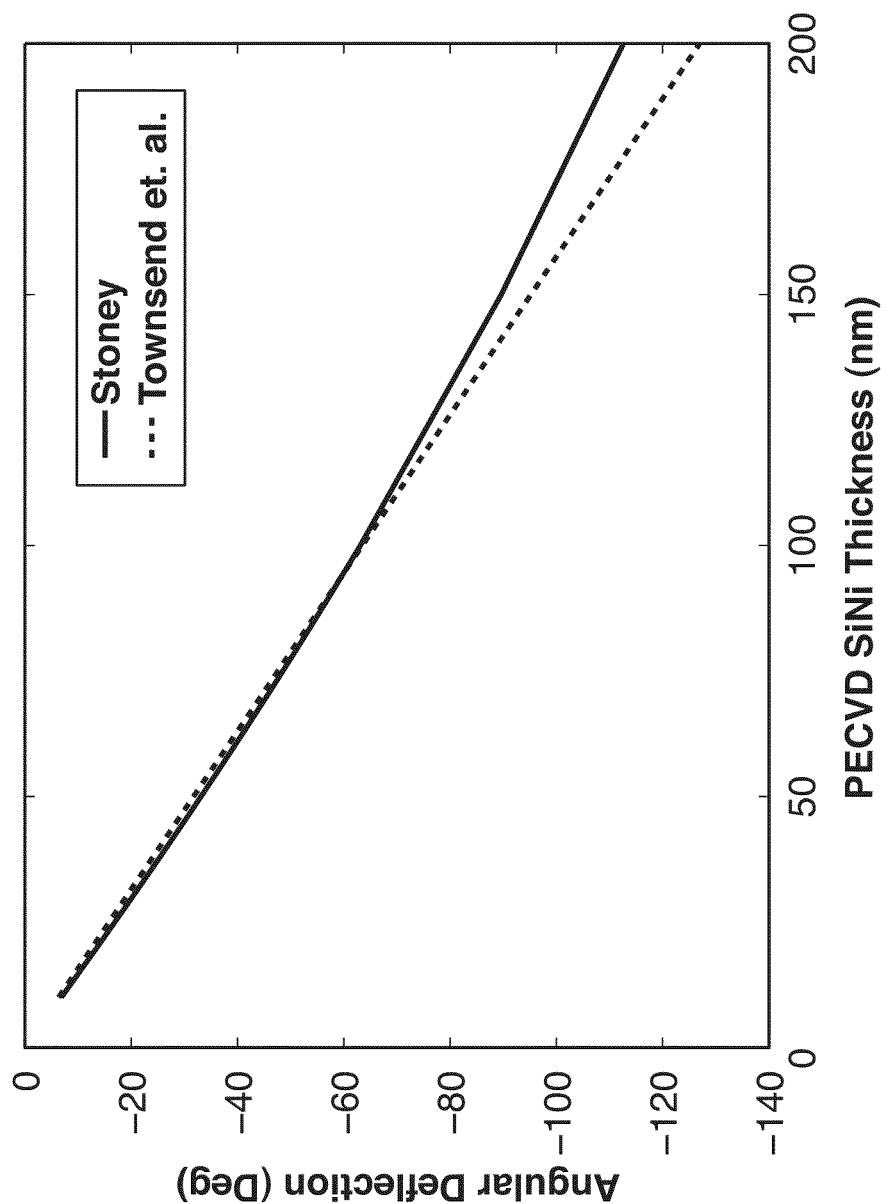
FIG. 9 shows the angular deflection of a silicon nitride beam as a function of thickness of the PECVD silicon nitride layer deposited on top.

FIG. 9 shows the angular deflection of a 600-µm-long, 1-µm-thick LPCVD silicon nitride beam (e.g. structural beam layer 64) as a function of thickness of the PECVD silicon nitride layer deposited on top (e.g. 1 GPa compressed layer 62). Note deflection increases with silicon nitride layer (e.g. layer 62) thickness, and that approximately −60° deflection can be achieved with a PECVD silicon nitride of 100 nm.

Figure 10:
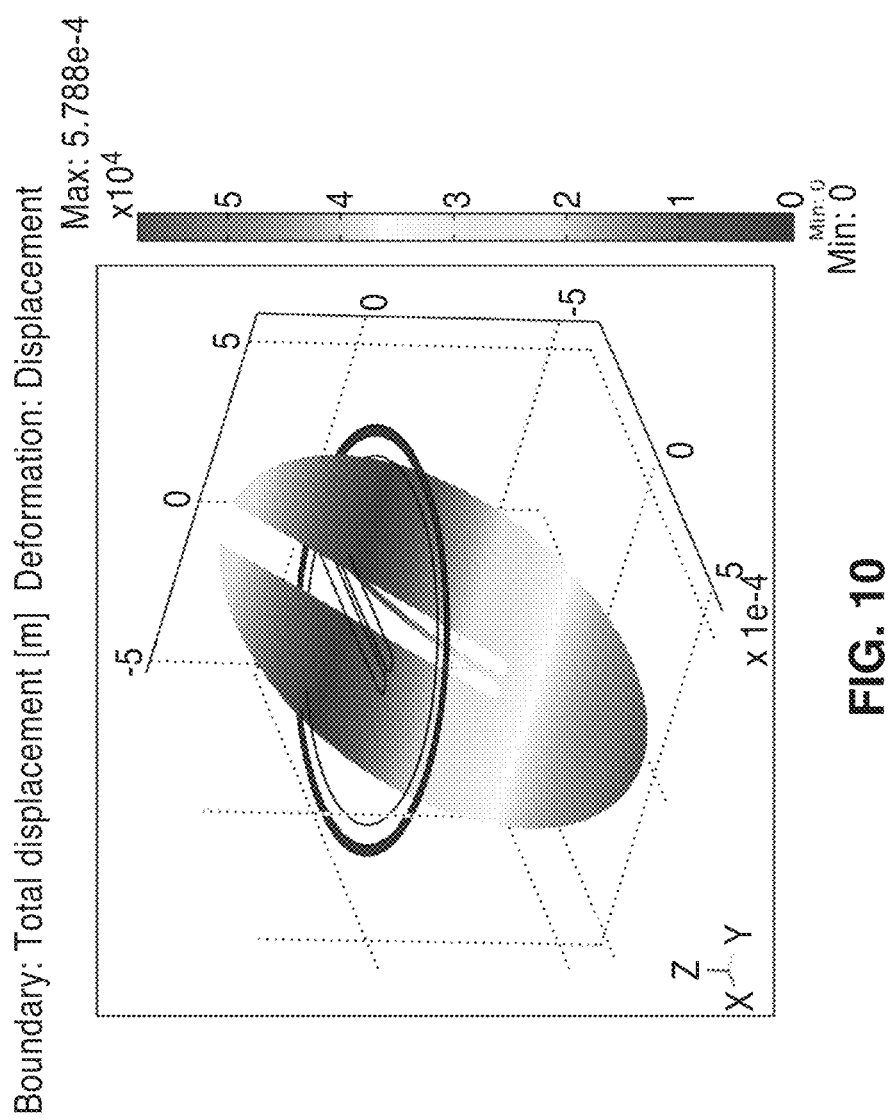
FIG. 10 shows a 3D COMSOL simulation of bending using a finite element analysis of a microactuator assembly of the present invention.

FIG. 10 shows a 3D COMSOL simulation of bending using a finite element analysis. A cantilever-based magnetic microactuator with a round structural activation plate, such as that shown in FIG. 5A and FIG. 5B, was used for simulation. Simulation parameters are shown in Table 1. Note that the maximum deflection at the tip of the cantilever is approximately 579 µm, corresponding to an angle ϕ=57°.

Figure 11:
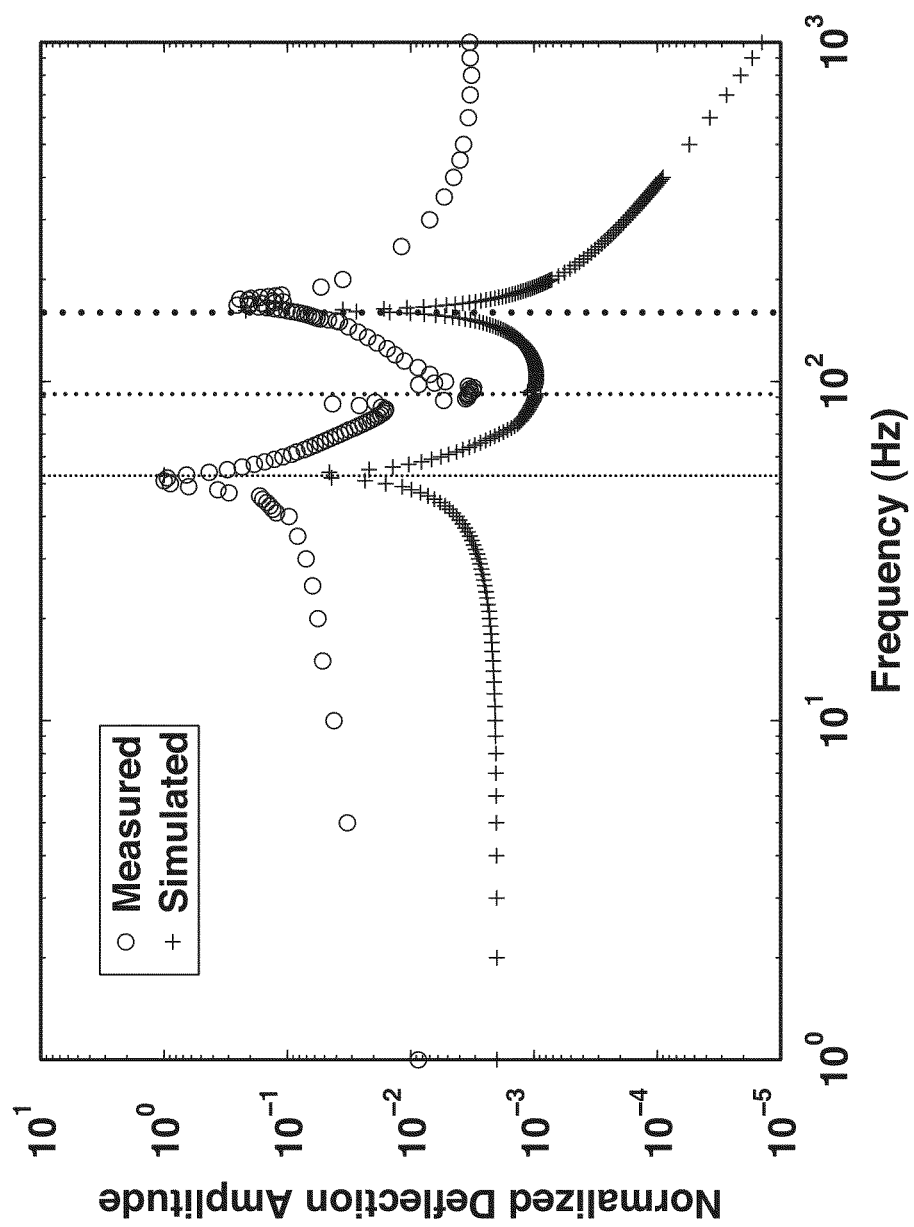
FIG. 11 is a plot of the simulated and measured deflection amplitude as a function of frequency.

The amount of post-release bend was measured using optical methods. FIG. 11 is a plot of the simulated and measured deflection amplitude as a function of frequency. Table 2 provides further data of the simulated and measured tests. The results indicate a very good control of the beam bending using the fabrication method detailed below.

FIG. 12A through FIG. 12J is a schematic diagram of an exemplary fabrication process for creating a round single-cantilever microactuator similar to that shown in FIG. 5A and FIG. 5B. It is appreciated that the same or similar process steps may be used to generate the multi interdigitated cantilever-based magnetic microactuators 200 of FIG. 7A through FIG. 8D by modifying the various masks.

Figure 12A:
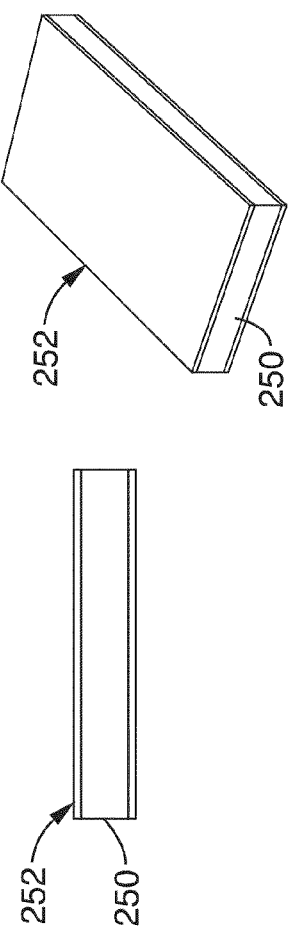
Figure 12B:
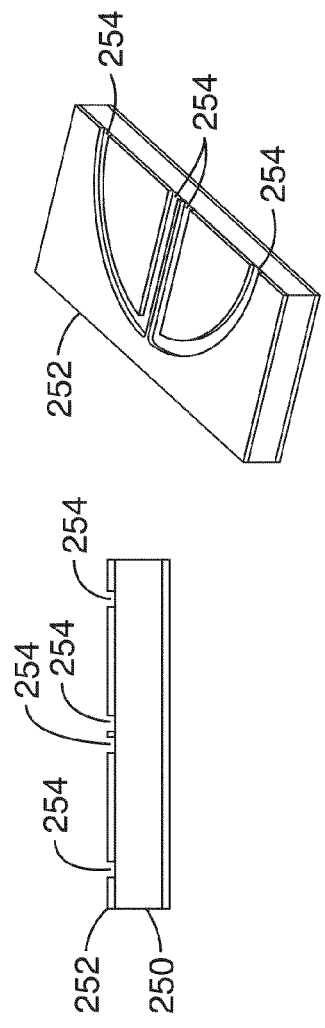

In the step shown in FIG. 12A, a layer 252 of silicon nitride (e.g. 1 µm thick LPCVD $Si_xN_y$) is applied to a substrate 250 (e.g. 500 µm thick silicon). Next, at the step shown in FIG. 12B, the cantilever and actuation plate structure is defined via a first mask to etch trenches 254 in the structural layer 252. Next, in the step shown in FIG. 12C, the compressed stress-inducing PECVD silicon-nitride layer 256 is generated on the cantilever section by use of a second mask and deposition of PECVD $Si_xN_y$ (e.g. 100 nm thick).

At the step shown in FIG. 12D, a third mask is applied to generate a liftoff chrome/niCr/Ni (e.g. 10 nm/200 nm thick) seed layer 258 the site of the actuation plate. At the step shown in FIG. 12E, a titanium conduction layer 260 is evaporated. Then, at the step shown in FIG. 12F, a fourth mask is used to electroplate a ferromagnetic element 262 (e.g. 7 µm thick Ni) on to the actuator plates. Next, at the step shown in FIG. 12G, a silicon dioxide ($SiO_2$) layer 266 (e.g. 2 µm thick) is deposited on the lower surface, and a polyimide layer (e.g. 2 µm thick) is deposited on the upper surface. At the step shown in FIG. 12H, the backside 270 is defined with a bulk-etch fifth mask. At the step shown in FIG. 12I the backside 270 is undercut to remove silicon from the substrate 250 via a deep reactive ion etching (DRIE) process. Finally, at the step shown in FIG. 12J, the polymide layer 264 is removed to release the cantilevered structure.

The MEMS actuation device of the present invention may be readily integrated into commercially available catheter systems, or part of a specifically designed catheter to produce catheters that can be implanted using existing surgical techniques.

Catheters (e.g. ventricular catheter 100) may vary in lumen diameter and thickness, as well as pore hole size, number, and placement. For hydrocephalus, commercially available catheters generally comprise a silicone rubber tube with integrated pore holes to allow fluid movement. The microfabrication process of the present invention provides a significant degree of customization to be compatible with wide range of geometric constraints. Moreover, the inherent batch-fabrication capabilities of the microfabrication process of the present invention allows for lower-cost per device.

A key metric in determining the effectiveness of a chronically implanted catheter is to measure the device lifetime. Although state-of-the-art catheters employ surface treatments to repel bacteria and cellular adhesion, the effectiveness these surface-modified catheters has yet to be tested in long-term studies with successful results. A surface coating may show promising short-term results, however, it often cannot sustain its effectiveness for a long period of time (years). With increasing life-expectancy, the chronically implanted catheters are expected to function properly for decades (often greater than 50 years in pediatric patients). As such, surface treatment alone is not an ideal solution to the longevity of the implanted catheters.

The microfabricated MEMS-enabled self-clearing catheters of the present invention provide a device for actively managing the long-term cellular occlusion problems of conventional catheters. Periodic actuations of the magnetic microactuators (e.g. microactuators 50, 100) physically removes any cellular accumulation and refreshes the pore to its initial clear state. Initial testing showed that a microactuators can be subjected to over 250 million cycles of actuation without showing any significant change in its mechanical property.

The cantilever-based microactuators of the present invention use the mechanical properties of a bimorph to create magnetic microactuators that will bend into the lumen of the catheter at rest. This bending reduces the obstruction that is present at rest and improves the normal flow of CSF compared to that of the torsional magnetic microactactuators. The miniaturized actuator then, in the presence of a magnetic field, can sweep across the pore thereby continually restoring the catheter patency after each actuation period.

A catheter incorporating the microactuators 50, 200 of the present invention can be implanted without additional training for the surgeon.

Although methods and devices of the present invention are particularly useful for the treatment of hydrocephalus, it is contemplated that these devises may be used for any application where a self-clearing catheter is desired.

From the discussion above it will be appreciated that the invention can be embodied in various ways, including the following:

1. An apparatus for self-clearing a flow pore in a human implant, comprising: a housing configured to be disposed in a flow pore of the implant; said housing comprising a central bore spanning between an upper surface and a lower surface of the housing, the central bore providing fluid communication into said flow pore; and an actuator plate extending from the upper surface of the housing into the central bore via a cantilever beam; the cantilever beam having a first end emanating at the central bore and a second end terminating at the actuator plate; the actuator plate configured to reciprocate within the central bore between a first position extending downward at an angle into the central bore and a second position substantially at or above the upper surface of the housing; wherein the cantilever beam is stressed such that it is preloaded to nominally curve downward to extend the actuator plate in the second position; and wherein the actuator plate comprises a magnet responsive to magnetic field such that the magnetic field drives the actuator plate toward the first position.

2. An apparatus as recited in embodiment 1, wherein in the second position the actuator plate and cantilever beam are configured to be substantially parallel with the upper surface.

3. An apparatus as recited in embodiment 2, wherein in the actuator plate is shaped and sized such that it covers a substantial portion of the central bore in the second position.

4. An apparatus as recited in embodiment 1: wherein in the cantilever beam comprises a composite material having a first low-stress layer and a second compressed layer; and wherein the second compressed layer preloads the cantilever beam to nominally curve in the first position.

5. An apparatus as recited in embodiment 4, wherein the second layer is sized to have a thickness that controls the angle at which the actuator plate extends into the bore.

6. An apparatus as recited in embodiment 4, wherein the second layer comprises PECVD silicon nitride.

7. An apparatus as recited in embodiment 6, wherein the first layer comprises LPCVD silicon nitride.

8. An apparatus as recited in embodiment 4, wherein the first layer of the cantilever beam, the actuator plate, and the upper surface of the housing are all micro-machined from one contiguous layer of material.

9. An apparatus as recited in embodiment 1, further comprising: a second actuator plate extending from the upper surface of the housing into the central bore via a second cantilever beam; wherein the second actuator plate extends from an opposing end of the central bore from the first actuator plate such that second actuator plate is interdigitating with said first actuator plate.

10. An apparatus as recited in embodiment 9, wherein the first actuator plate is magnetically charged in a different direction than the first actuator plate, such that the magnetic field causes the second actuator to curve in an opposite direction than the first actuator plate.

11. A self-clearing ventricular catheter, comprising: a catheter body comprising a central lumen extending from a proximal end to a distal end of the catheter; one or more pores providing fluid communication into the central lumen of the catheter body; wherein the one or more pores comprise a central bore extending from an external surface of the catheter to an internal surface of the catheter; the one or more pores comprising a self-clearing actuator; the actuator extending into the central bore via a cantilever beam; the cantilever beam having a first end emanating at the central bore and a second end terminating at the actuator; the actuator configured to reciprocate within the central bore between a first position extending downward at an angle into the central bore and a second position substantially at or above the external surface of the catheter; wherein the cantilever beam is stressed such that it is preloaded to nominally curve downward to extend the actuator into the second position; and wherein the actuator comprises a magnet responsive to magnetic field such that the magnetic field drives the actuator toward the first position.

12. A ventricular catheter as recited in embodiment 11, wherein in the second position the actuator and cantilever beam are configured to be substantially parallel with the external surface.

13. A ventricular catheter as recited in embodiment 11: wherein in the cantilever beam comprises a composite material having a first low-stress layer and a second compressed layer; and wherein the second compressed layer preloads the cantilever beam to nominally curve in the first position.

14. A ventricular catheter as recited in embodiment 13, wherein the second layer is sized to have a thickness that controls the angle at which the actuator plate extends into the bore.

15. A ventricular catheter as recited in embodiment 13, wherein the second layer comprises PECVD silicon nitride and the first layer comprises LPCVD silicon nitride.

16. A ventricular catheter as recited in embodiment 11, further comprising: a second actuator extending from the upper surface of the housing into the central bore via a second cantilever beam; wherein the second actuator extends from an opposing end of the central bore from the first actuator such that second actuator is interdigitating with said first actuator.

17. A ventricular catheter as recited in embodiment 16, wherein the first actuator is magnetically charged in a different direction than the first actuator, such that the magnetic field causes the second actuator to curve in an opposite direction than the first actuator.

18. A shunt system configured for diverting cerebrospinal fluid (CSF) from a ventricle of the brain, comprising: a ventricular catheter having proximal end and a distal end; tubing coupled to the distal end of the ventricular catheter; said tubing having a length sufficient to extend from the ventricle into an abdominal region of the patient; the ventricular catheter comprising a central lumen extending from a proximal end to a distal end of the catheter; the ventricular catheter comprising one or more pores each comprising a central bore extending from an external surface of the catheter to an internal surface of the catheter; the one or more pores providing fluid communication of CSF from the ventricle into the central lumen of the catheter; the one or more pores comprise a self-clearing actuator; the actuator extending into the central bore via a cantilever beam; the cantilever beam having a first end emanating at the central bore and a second end terminating at the actuator; the actuator configured to reciprocate within the central bore between a first position extending downward at an angle into the central bore and a second position substantially at or above the external surface of the catheter; wherein the cantilever beam is stressed such that it is preloaded to nominally curve downward to extend the actuator into the second position; and wherein the actuator comprises a magnet responsive to magnetic field such that the magnetic field drives the actuator toward the first position.

19. A system as recited in embodiment 18, wherein in the second position the actuator and cantilever beam are configured to be substantially parallel with the external surface.

20. A system as recited in embodiment 19: wherein in the cantilever beam comprises a composite material having a first low-stress layer and a second compressed layer; and wherein the second compressed layer preloads the cantilever beam to nominally curve in the first position.

21. A system as recited in embodiment 18, further comprising: a second actuator extending from the upper surface of the housing into the central bore via a second cantilever beam; wherein the second actuator extends from an opposing end of the central bore from the first actuator such that second actuator is interdigitating with said first actuator.

22. A system as recited in embodiment 21, wherein the first actuator is magnetically charged in a different direction than the first actuator, such that the magnetic field causes the second actuator to curve in an opposite direction than the first actuator.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Simulation Parameters For COMSOL Simulation

|  | Structural Layer (LPCVD) | Stress Layer (PECVD) |
|---|---|---|
| Elastic Modulus | 250 GPa | 110 GPa |
| Intrinsic Stress | 200 MPa | −1 GPa |
| Length | 650 µm | 650 µm |
| Width | 20 µm | 20 µm |
| Thickness | 1 µm | 100 nm |

TABLE 2

Frequencies For Simulated And Measured Deflection Amplitude

|  | $1^{st}$ | $2^{nd}$ | $3^{rd}$ |
|---|---|---|---|
| Simulated | 53 Hz | 92 Hz | 162 Hz |
| Measured | 51 Hz | 87 Hz | 175 Hz |

What is claimed is:

1. An apparatus for self-clearing a flow pore in a human implant, comprising:
    a housing configured to be disposed in a flow pore of the implant;
    said housing comprising a central bore spanning between an upper surface and a lower surface of the housing, the central bore providing fluid communication into said flow pore; and
    an actuator plate extending from the upper surface of the housing into the central bore via a cantilever beam;
    the cantilever beam having a first end emanating at the central bore and a second end terminating at the actuator plate;
    the actuator plate configured to reciprocate within the central bore between a first position extending downward at an angle into the central bore and a second position substantially at or above the upper surface of the housing;
    wherein the cantilever beam is stressed such that it is preloaded to nominally curve downward to extend the actuator plate in the first position;
    wherein the actuator plate comprises a magnet responsive to magnetic field such that the magnetic field drives the actuator plate toward the second position;
    wherein in the cantilever beam comprises a composite material having a first low-stress layer and a second compressed layer; and
    wherein the second compressed layer preloads the cantilever beam to nominally curve in the first position.

2. An apparatus as recited in claim 1, wherein in the second position the actuator plate and cantilever beam are configured to be substantially parallel with the upper surface.

3. An apparatus as recited in claim 2, wherein the actuator plate is shaped and sized such that it covers a substantial portion of the central bore in the second position.

4. An apparatus as recited in claim 1, wherein the second layer is sized to have a thickness that controls the angle at which the actuator plate extends into the bore.

5. An apparatus as recited in claim 1, wherein the second layer comprises PECVD silicon nitride.

6. An apparatus as recited in claim 5, wherein the first layer comprises LPCVD silicon nitride.

7. An apparatus as recited in claim 1, wherein the first layer of the cantilever beam, the actuator plate, and the upper surface of the housing are all micro-machined from one contiguous layer of material.

8. An apparatus as recited in claim 1, further comprising:
   a second actuator plate extending from the upper surface of the housing into the central bore via a second cantilever beam;
   wherein the second actuator plate extends from an opposing end of the central bore from the first actuator plate such that second actuator plate is interdigitating with said first actuator plate.

9. An apparatus as recited in claim 8, wherein the first actuator plate is magnetically charged in a different direction than the first actuator plate, such that the magnetic field causes the second actuator to curve in an opposite direction than the first actuator plate.

* * * * *